US005416939A

United States Patent [19]

Maalouli

[11] Patent Number: 5,416,939

[45] Date of Patent: May 23, 1995

[54] TILTING BED APPARATUS

[76] Inventor: Raja G. Maalouli, 1793 N. Allen Ave., Pasadena, Calif. 91104

[21] Appl. No.: 183,861

[22] Filed: Jan. 21, 1994

[51] Int. Cl.[6] .......... A61G 7/00; A61F 5/00

[52] U.S. Cl. .......... 5/610; 5/615; 5/624; 5/651; 128/845; 482/142; 482/144; 606/244

[58] Field of Search .......... 5/610, 615, 651, 624, 5/600, 608, 648; 606/240, 244; 128/845, 846; 482/142, 146, 145, 144, 140

[56] References Cited

U.S. PATENT DOCUMENTS

| | | | |
|---|---|---|---|
| 3,081,085 | 3/1963 | De Girolamo | 482/144 |
| 3,794,023 | 2/1974 | Bradley | 606/244 |
| 4,442,832 | 4/1984 | Ollenberger | 606/244 |
| 4,582,050 | 4/1986 | Willis | 5/610 |
| 4,739,749 | 4/1988 | Lindley | 606/244 |
| 4,802,249 | 2/1989 | Bills . | |
| 4,819,282 | 4/1989 | McArthur et al. | 5/610 |
| 4,847,929 | 7/1989 | Pupovic . | |
| 4,873,731 | 10/1989 | Williamson . | |
| 4,942,633 | 7/1990 | Thomas et al. | 5/11 |
| 4,996,731 | 3/1991 | Kruyt . | |
| 5,243,726 | 9/1993 | Bisbee | 5/610 |

*Primary Examiner*—Alexander Grosz

[57] ABSTRACT

An apparatus wherein a framework is arranged to pivotally mount a bed structure including a mattress to permit an individual to elevate the feet portion of the individual relative to the head. The feet of the individual are secured within a strap structure, with the strap structure rotatably mounted relative to a rotary support. The tilting bed apparatus allows a person to sleep in a tilted position, whereby beneficial effects of gravity, such as increased blood flow to the brain and reduced spinal column compression, may be obtained.

4 Claims, 4 Drawing Sheets

TILTING BED APPARATUS

BACKGROUND OF THE INVENTION

1. Field of the Invention

The field of invention relates to tilting bed apparatus, and more particularly pertains to a new tilting bed apparatus arranged for the ease of elevating an individual's feet relative to the head portion of the individual.

2. Description of the Prior Art

Tilting bed structure of various types are indicated in the prior art and exemplified by U.S. Pat. Nos. 4,996,731; 4,873,731; 4,942,633; and 4,847,929. The instant invention attempts to overcome deficiencies of the prior art by providing a tilting bed structure arranged for the ease of tilting and positioning thereof of the mattress structure of a bed and to further provide for sleeping in a partially inverted position. In these respects, the present invention substantially fulfills this need.

SUMMARY OF THE INVENTION

In view of the foregoing disadvantages inherent in the known types of tilting bed apparatus now present in the prior art, the present invention provides a tilting bed apparatus including a mattress arranged for pivotal mounting relative to a support frame and providing means for rotatably mounting an individual's feet relative to the mattress. As such, the general purpose of the present invention, which will be described subsequently in greater detail, is to provide a new tilting bed apparatus and method which has many of the advantages of the prior art listed heretofore and many novel features that result in a tilting bed apparatus which is not anticipated, rendered obvious, suggested, or even implied by any of the prior art, either alone or in any combination thereof.

To attain this, the present invention provides an apparatus wherein a framework is arranged to pivotally mount a bed structure including a mattress to permit an individual to elevate the feet portion of the individual relative to the head. The feet of the individual are secured within strap structure, with the strap structure rotatably mounted relative to a rotary support. The tilting bed apparatus allows a person to sleep in a tilted position, whereby beneficial effects of gravity, such as increased blood flow to the brain and reduced spinal column compression, may be obtained.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

Those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing Abstract is to enable the U.S. Patent and Trademark office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new tilting bed apparatus and method which has many of the advantages of the prior art listed heretofore and many novel features that result in a tilting bed apparatus which is not anticipated, rendered obvious, suggested, or even implied by any of the prior art, either alone or in any combination thereof.

It is a further object of the present invention to provide a new tilting bed apparatus which is of a durable and reliable construction.

An even further object of the present invention is to provide a new tilting bed apparatus which is susceptible of a low cost of manufacture with regard to both materials and labor, and which accordingly is then susceptible of low prices of sale to the consuming public, thereby making such tilting bed apparatuses economically available to the buying public.

Still yet another object of the present invention is to provide a new tilting bed apparatus which provides in the apparatuses and methods of the prior art some of the advantages thereof, while simultaneously overcoming some of the disadvantages normally associated therewith.

A still further object of the present invention is to provide a tilting bed apparatus which allows a person to sleep in a tilted position, whereby beneficial effects of gravity, such as increased blood flow to the brain and reduced spinal column compression, may be obtained.

An even further object of the present invention is to provide a tilting bed apparatus including a mattress arranged for pivotal mounting relative to a support frame and additionally to provide means for rotatably mounting an individual's feet relative to the mattress.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein.

DESCRIPTION OF THE PREFERRED EMBODIMENT

Figure 1:
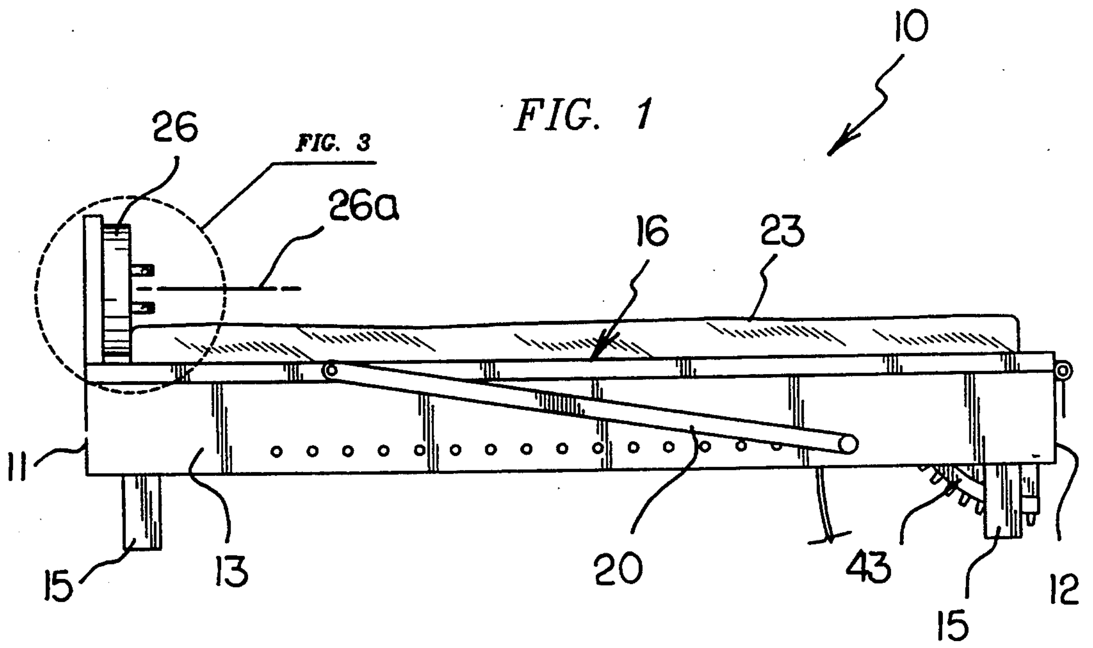
FIG. 1 is a side elevation view of the invention.

With reference now to the drawings, and in particular to FIGS. 1–6 thereof, a new tilting bed apparatus embodying the principles and concepts of the present invention and generally designated by the reference numeral 10 will be described.

More specifically, the tilting bed apparatus 10 of the instant invention comprises support framework including a first end wall 11 spaced from a second end wall 12, with a pair of spaced side walls 13 extending therebetween. At least one of the side walls 13, and preferably both of the side walls, includes a row of side wall apertures 14 oriented between the first and second end walls 11 and 12. Support legs 15 extend from the comer intersection of the side walls with the first and second end walls to space the side walls and end walls above an underlying support, such as a floor or the like.

A bed frame 16 having bed frame side rails 17 and a first end rail 18 spaced from a second end rail 19 is provided. The second end rail 19 includes a frame hinge **16*a* mounted to the second end rail and to the second end wall 12 to hingedly mount in a pivotal relationship the bed frame 16 relative to the side walls 13. A support leg 20 having first and second ends includes a pivot axle 21 pivotally mounting the support leg 20 to one of the side rails 17, with the second end of the support leg 20 having a peg 22 received selectively with one of the side wall apertures 14. It may be desirable to employ support leg 20 mounted to each of the bed frame side rails 17**, in a manner as illustrated in FIG. 2, to provide for additional support.

A mattress pad 23 is arranged for securement to the bed frame 16. Spaced hook and loop fastener strips 24 are mounted onto the bed frame side rails 17 and arranged for selective securement to the mattress pad 23 that in turn is formed of a fibrous material to permit adherence of the hook and loop fastener strips 24, thereby selectively securing the mattress pad to the frame 16.

Figure 2:
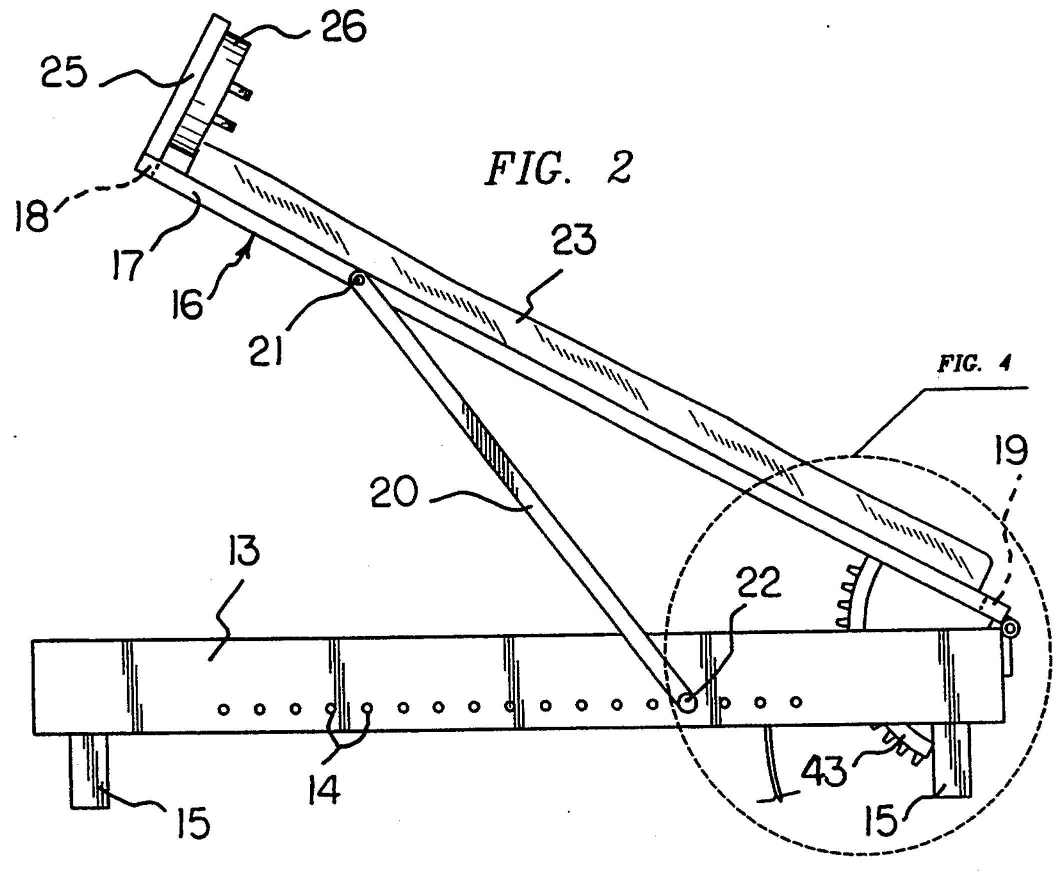
FIG. 2 is further side elevation view of the invention arranged in a tilting orientation of the mattress relative to the support frame structure.
Figure 3:
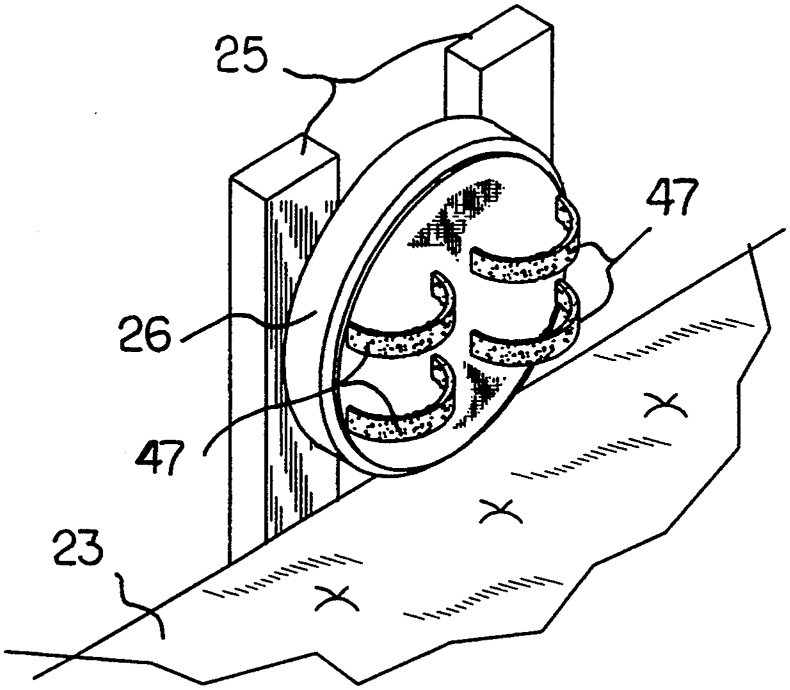
FIG. 3 is an enlarged isometric illustration of section 3 as set forth in FIG. 1.

Mounting legs 25 are provided and are fixedly mounted to the first end rail 18 to extend upwardly therefrom beyond the mattress pad 23, as best illustrated in FIGS. 2 and 3. The mounting legs 25 support a cylindrical container 26 which is mounted in a fixed relationship relative to the mounting legs. The cylindrical container includes a cylindrical container axis **26*a*, as shown in FIG. 1, which is substantially parallel relative to the mattress pad 23**.

Figure 5:
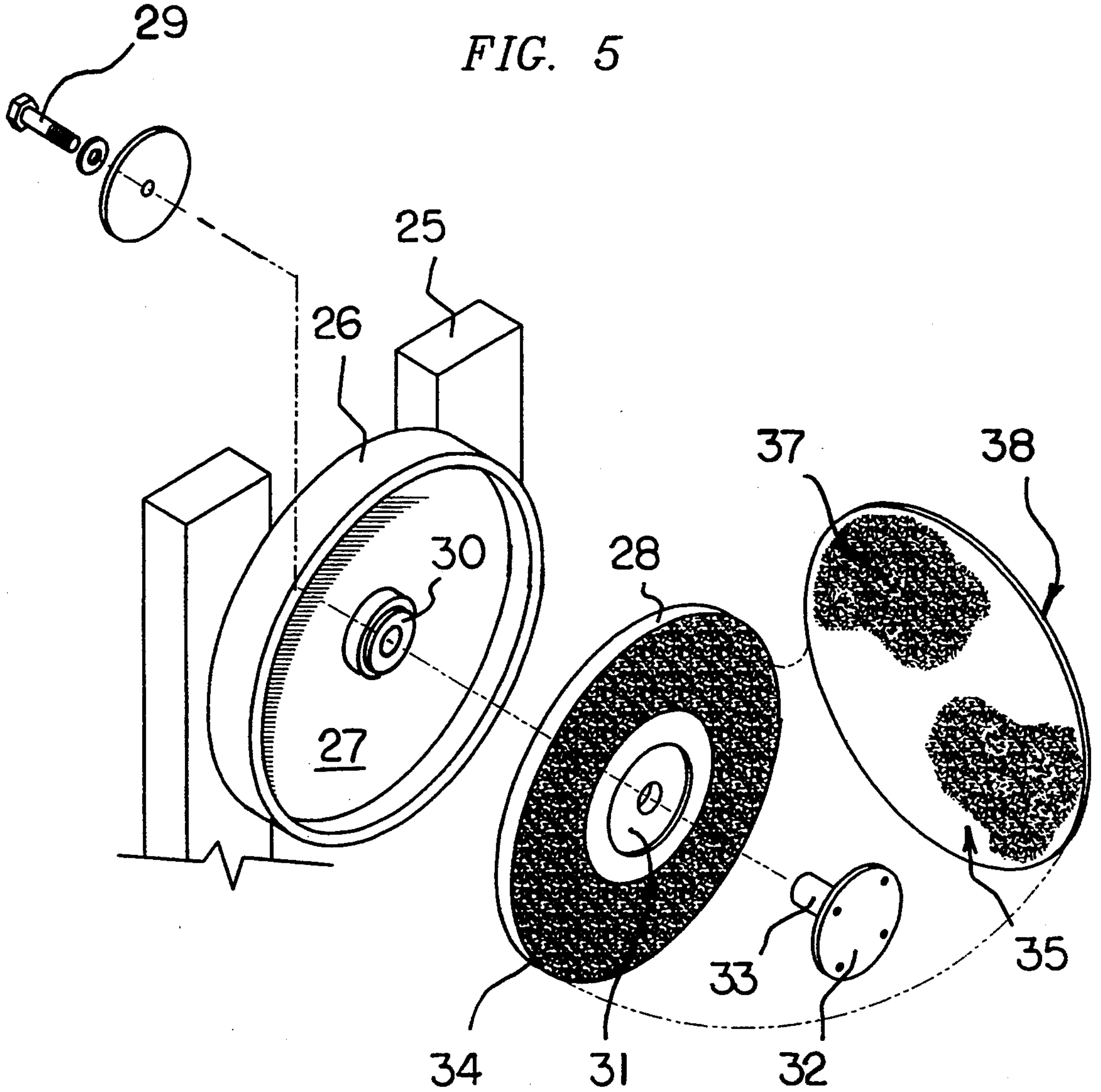
FIG. 5 is an exploded isometric illustration of the rotary foot support structure.
Figure 6:
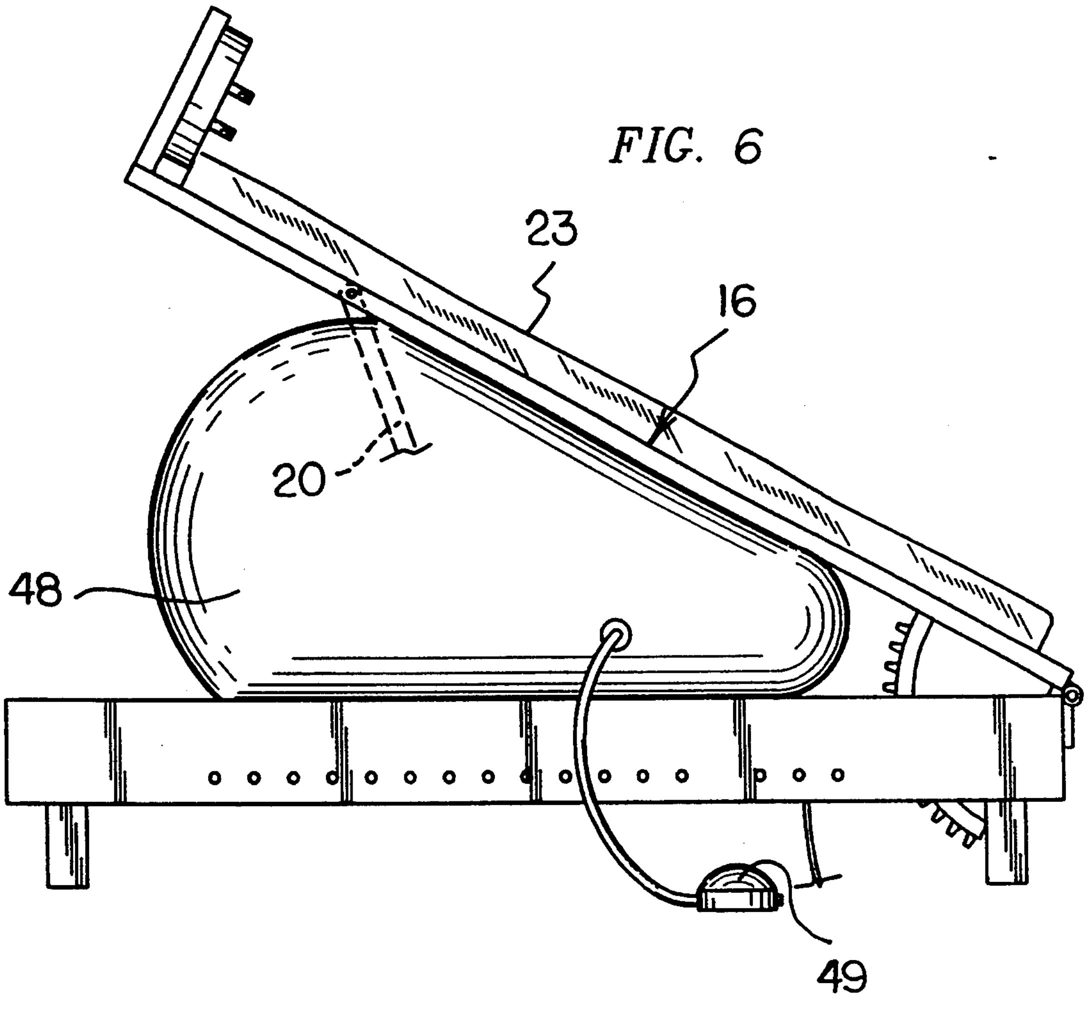
FIG. 6 is a side elevation view of a pneumatic side lift chamber as employed by the invention.

With reference now to FIG. 5, it can be shown that the cylindrical container 26 further includes a container floor 27 receiving a support disc 28 thereon. The support disc 28 is rotatably mounted about a support disc axle 29 that is directed coaxially through an aperture in the container floor aligned with the axis **26*a*. The axle is provided with a bearing 30 interposed between the container floor 27 and the support disc 28 to permit free rotation of the support disc 28 with respect to the cylindrical container 26. The support disc is provided with a central recess 31 arranged to receive a flange 32 therewithin. A tube 33 is fixedly mounted to the flange 32, with the tube 33 projecting through the both support disc 28 and through the container floor 27 to engage the support disc axle 29 while rotatably capturing the support disc therebetween. In this manner, the flange 32 provides a stable rotative mounting of the support disc 28 relative to the container floor 27**.

The support disc 28 includes a support disc hook and loop fastener surface 34 arranged for securement to a resilient pad 35. More specifically, the rear wall 37 of the resilient pad is provided with a hook and loop rear wall surface, as illustrated in FIG. 5. The resilient pad 35 includes a front wall 38 having plural pairs of straps 47 (see FIG. 3) to receive an individual's feet therethrough for securement of the individual to the resilient pad 35, as well as to the cylindrical container 26. In this manner, a person may secure his feet within the straps 47, whereby a tilting of the apparatus 10 may then be commenced. When a desired angle has been reached, the support legs may be engaged to corresponding side wall apertures to secure such an angle. The person may then comfortably sleep at such inclined angle and, because of the rotational mounting of the straps as described above, even turn or rotate into any desired position. In addition, is contemplated that cooperative footwear and releasable mounting plates be secured to the support disc in place of the foot straps to effect a more secure engagement between the person and the support disc.

Figure 4:
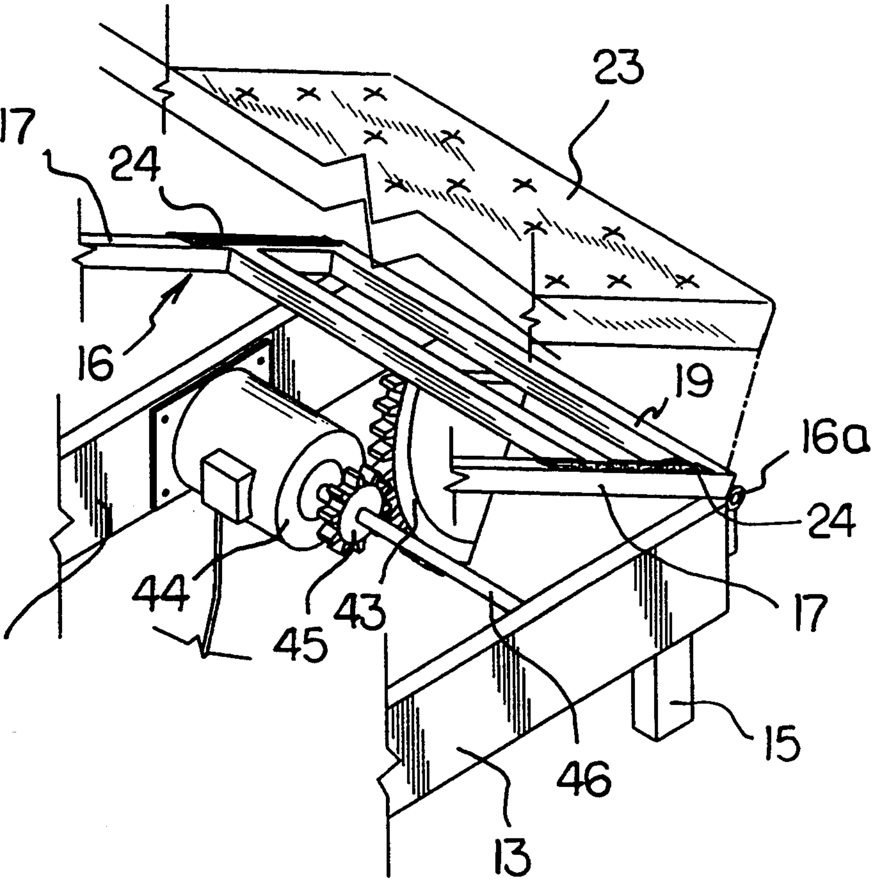
FIG. 4 is an enlarged isometric illustration, partially in an exploded view, of section 4 as set forth in FIG. 2.

To effect a tilting of the apparatus, a pivoting means is provided. FIG. 4 indicates the use of a gear sector 43 fixedly mounted to the bed frame 16, such that the gear sector cooperates with a drive motor 44 having a drive motor gear 45, with the drive motor gear 45 rotatably mounted about a drive motor axle 46, such that upon rotation of the drive motor gear 45 effects pivoting of the bed frame 16 into a desired position.

Additionally or alternatively, if desired, the pivoting means may take the form of a pneumatic chamber 48 oriented between the bed frame 16 and the side walls 13 of the support structure, as indicated in FIG. 7, such that inflation of the mounting chamber 48 by a manual or electric pump 49 effects positioning of the bed frame in a pivoted orientation in lieu of or in addition to the use of the support legs 20.

As to the manner of usage and operation of the instant invention, the same should be apparent from the above disclosure, and accordingly no further discussion relative to the manner of usage and operation of the instant invention shall be provided.

With respect to the above description then, it is to be realized that the optimum dimensional relationships for the parts of the invention, to include variations in size materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by LETTERS PATENT of the United States is as follows:

1. A tilting bed apparatus, comprising:

a support framework having a first end wall spaced from a second end wall with a pair spaced side walls coupled to the end walls and extending between the first and second end walls, at least one of said side walls including a row of side wall apertures extending between the first end wall and the second end wall;

a plurality of support legs mounted to the support framework and extending below the support framework;

a bed frame having a bed frame first end rail spaced from a bed frame second end rail with a pair of spaced bed frame side rails coupled to the end rails and extending between the first and second end rails;

a hinge secured to the bed frame second end rail and secured to the second end wall;

a support leg having a first end spaced from a second end;

pivot axle pivotally mounting the support leg at the first end thereof to one of said side rails;

a peg positioned at the second end of the support leg and being removably received within one of said side wall apertures;

a mattress pad mounted onto said bed frame and being positioned coextensively of the bed frame between the first end rail and the second end rail; and, pivoting means for pivoting the bed frame relative to the support framework about the hinge.

2. The apparatus as set forth in claim 1, wherein the pivoting means includes a gear sector fixedly mounted to the bed frame; a drive motor mounted between the side walls, the drive motor including a drive motor axle; a drive motor gear operatively coupled to the drive motor axle, the drive motor gear being in mesh with the gear sector, whereupon rotation of the drive motor gear effects displacement of the gear sector and pivoting of the bed frame relative to the support framework.

3. The apparatus as set forth in claim 2, and further including at least one mounting leg fixedly secured to the bed frame first end rail, with the mounting leg having a cylindrical container secured thereto, the cylindrical container being oriented about an axis arranged parallel and spaced from the mattress pad, the cylindrical container having container floor; a support disc having an aperture surrounded by a central recess, the support disc being received within the cylindrical container spaced from the container floor; a support disc axle directed coaxially through the aperture in said support disc; a bearing interposed between the support disc and the container floor; a flange having a tube projecting therefrom, with the flange being received complementarily within the central recess such that the tube is directed through the aperture in the support disc to receive the axle therethrough, the support disc further having a support disc hook and loop fastener surface, with a resilient pad including a resilient pad rear wall and a resilient pad front wall, the resilient pad rear wall including a hook and loop fastener rear wall surface arranged for securement to the support disc hook and loop fastener surface, and the resilient pad front wall including a plurality of strap pairs mounted thereon for securement of an individual's feet thereto.

4. The apparatus as set forth in claim 3, including a pneumatic chamber interposed between the bed frame and the support framework, wherein the pneumatic chamber includes a pump arranged for inflation of the pneumatic chamber to pivot the bed frame relative to the support framework.

* * * * *